(12) United States Patent
Otsuka

(10) Patent No.: US 12,022,990 B2
(45) Date of Patent: Jul. 2, 2024

(54) ENDOSCOPE APPARATUS, FUNCTION LIMITATION METHOD, AND NON-TRANSITORY RECORDING MEDIUM HAVING PROGRAM RECORDED THEREIN

(71) Applicant: OLYMPUS CORPORATION, Tokyo (JP)

(72) Inventor: Yusuke Otsuka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 768 days.

(21) Appl. No.: 17/117,747

(22) Filed: Dec. 10, 2020

(65) Prior Publication Data

US 2021/0093156 A1 Apr. 1, 2021

Related U.S. Application Data

(63) Continuation of application No. PCT/JP2019/023073, filed on Jun. 11, 2019.

(30) Foreign Application Priority Data

Jun. 11, 2018 (JP) .................................. 2018-111466

(51) Int. Cl.
*A61B 1/00* (2006.01)

(52) U.S. Cl.
CPC ...... *A61B 1/00004* (2013.01); *A61B 1/00011* (2013.01); *A61B 1/0004* (2022.02); *A61B 1/00045* (2013.01)

(58) Field of Classification Search
CPC ............ A61B 1/00004; A61B 1/00011; A61B 1/00006; A61B 1/0004; A61B 1/00045; G06F 21/31; G06F 21/45
See application file for complete search history.

(56) References Cited

U.S. PATENT DOCUMENTS

2004/0243448 A1* 12/2004 Shoji ...................... G16H 30/20
　　　　　　　　　　　　　　　　　　　　　　　705/3
2006/0174133 A1* 8/2006 Obata ...................... G06F 21/31
　　　　　　　　　　　　　　　　　　　　　　　713/182

(Continued)

FOREIGN PATENT DOCUMENTS

CN　　　102341821 A　　2/2012
CN　　　105320278 A　　2/2016

(Continued)

OTHER PUBLICATIONS

"Method and Apparatus for Mobile Identity Authentication" - Authors et al.: Disclosed Anonymously, IP.com No. IPCOM000194545D, IP.com Electronic Publication Date: Mar. 29, 2010. (Year: 2010).*

(Continued)

*Primary Examiner* — Mainul Hasan
(74) *Attorney, Agent, or Firm* — Oliff PLC

(57) ABSTRACT

An endoscope apparatus that includes a storage memory storing first authentication information, a transmitter/receiver that performs communication with an endoscope, and an operational device. The operational device performs a process including acquiring the first authentication information stored in the storage memory and acquiring second authentication information stored in the endoscope connected to the endoscope apparatus from the endoscope. The operational device further performs determining whether the acquired first and second authentication information match each other, and limiting execution of at least some functions among a plurality of functions to be executed in cooperation with the endoscope in response to determining that the first and second authentication information do not match each other.

11 Claims, 7 Drawing Sheets

(56) References Cited

U.S. PATENT DOCUMENTS

| | | | |
|---|---|---|---|
| 2009/0247836 A1 | 10/2009 | Cole et al. | |
| 2013/0297343 A1* | 11/2013 | Hirose | G16H 30/40 |
| | | | 705/3 |
| 2016/0029943 A1 | 2/2016 | Mizuochi et al. | |
| 2017/0161439 A1* | 6/2017 | Raduchel | G16H 10/60 |
| 2017/0289133 A1* | 10/2017 | Yang | A63F 13/79 |

FOREIGN PATENT DOCUMENTS

| | | | |
|---|---|---|---|
| CN | 105592104 A | | 5/2016 |
| JP | H11-169338 A | | 6/1999 |
| JP | 2002-345723 A | | 12/2002 |
| JP | 2002345723 A | * | 12/2002 |
| JP | 2006-255192 A | | 9/2006 |
| JP | 2008-113713 A | | 5/2008 |
| JP | 2009-160312 A | | 7/2009 |
| JP | 2009271619 A | * | 11/2009 |
| JP | 2012-143464 A | | 8/2012 |
| JP | 2014-204892 A | | 10/2014 |
| JP | 2016077432 A | * | 5/2016 |
| JP | 2016-214490 A | | 12/2016 |

OTHER PUBLICATIONS

Sep. 3, 2019 International Search Report issued in International Patent Application No. PCT/JP2019/023073.
Jan. 9, 2024 Office Action issued in CN Patent Application No. 201980039542.0.

* cited by examiner

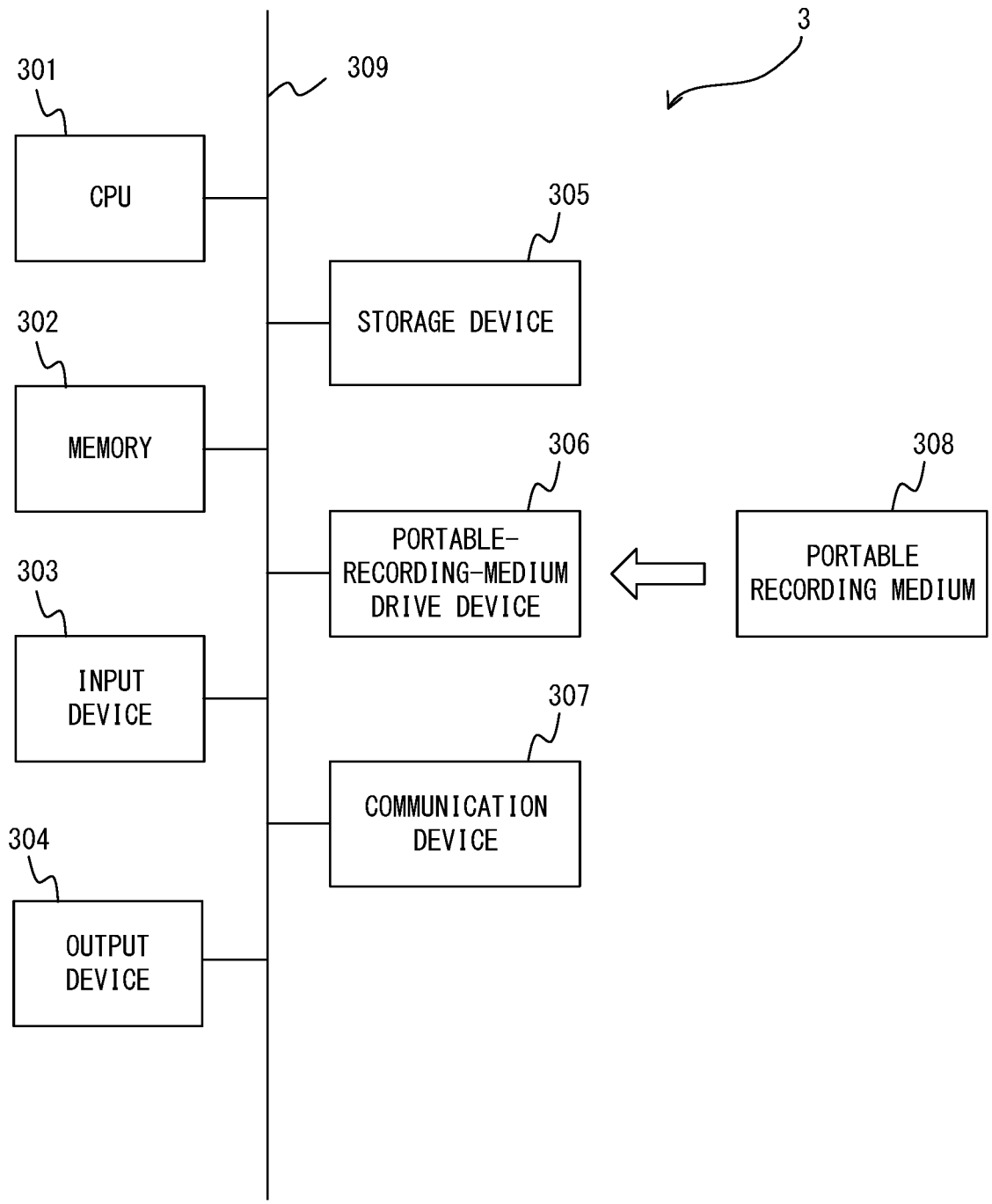
F I G. 2

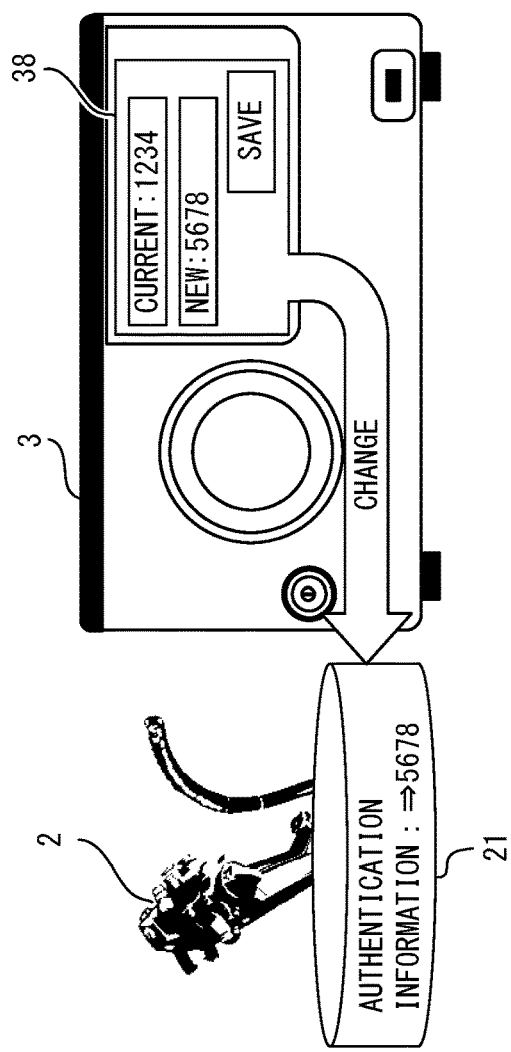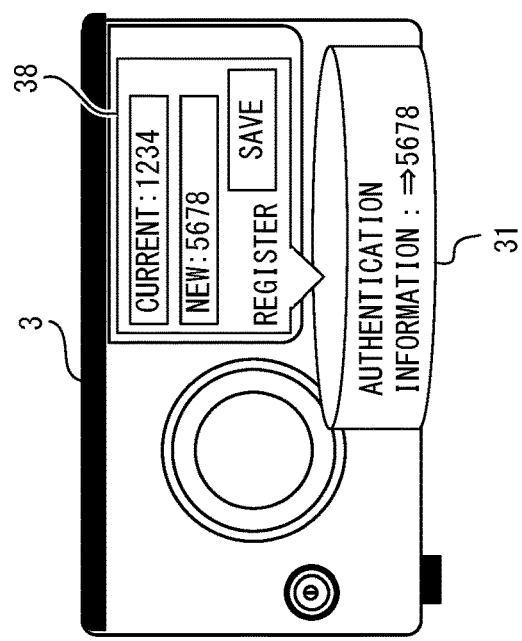
F I G. 4

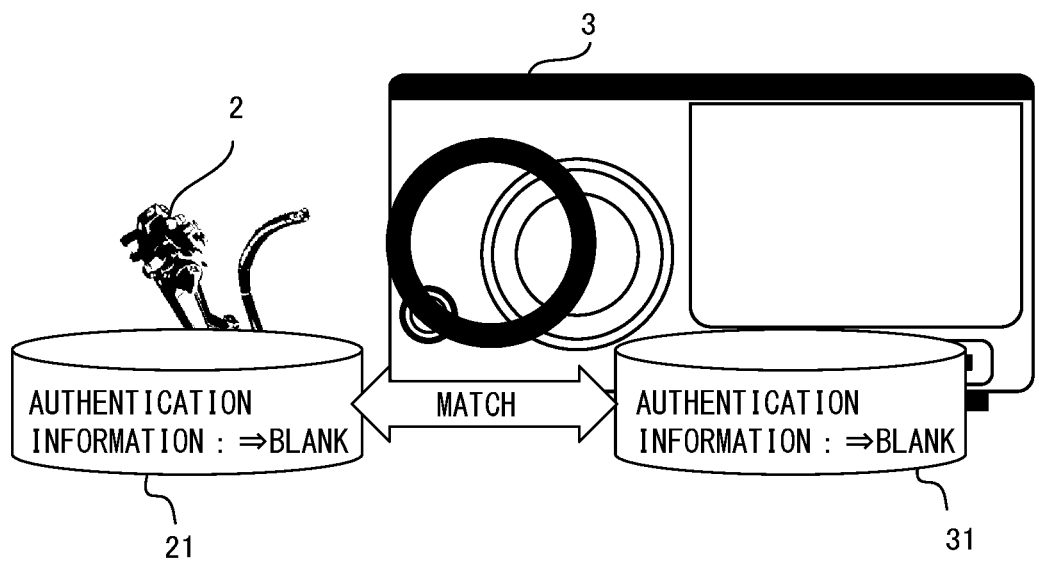
F I G. 7

ENDOSCOPE APPARATUS, FUNCTION LIMITATION METHOD, AND NON-TRANSITORY RECORDING MEDIUM HAVING PROGRAM RECORDED THEREIN

CROSS-REFERENCE TO RELATED APPLICATIONS

This application is based upon and claims the benefit of priority from prior Japanese Patent Application No. 2018-111466, filed Jun. 11, 2018, the entire contents of which are incorporated herein by this reference.

This application is a continuation application of International Application PCT/JP2019/023073 filed on Jun. 11, 2019, the entire contents of which are incorporated herein by reference.

TECHNICAL FIELD

The present embodiment(s) relates to an endoscope apparatus, a function limitation method implemented by the endoscope apparatus, and a non-transitory recording medium having recorded therein a program to be executed by a computer for the endoscope apparatus.

BACKGROUND

Endoscope systems have conventionally been known as medical systems.

An endoscope system includes an endoscope that captures images of the inside of a subject, an endoscope apparatus that generates a video signal by processing a signal output from the endoscope, and the like. The endoscope apparatus may be referred to as a video processor.

For example, the following techniques are known as techniques pertaining to limitations on the use of an endoscope system:

A technique wherein only certain operators are authorized to use an endoscope system so as to allow for management of, and security control for, the endoscope system; a technique wherein user authentication is carried out with an electronic endoscope system provided with an electronic endoscope that does not have a user authentication function, so that function limitations for the system can be attained; and a technique wherein illicit use of an endoscope by a renter can be prevented.

SUMMARY

In an aspect of an embodiment, an endoscope apparatus that includes a storage memory that stores first authentication information; a transmitter/receiver that performs communication with an endoscope connected to the endoscope apparatus; and an operational device that performs a process including: acquiring the first authentication information stored in the storage memory and acquiring, from the endoscope, second authentication information stored in the endoscope connected to the endoscope apparatus, the first authentication information and the second authentication information being different among facilities in which the endoscope and the endoscope apparatus are respectively located, determining whether the acquired first authentication information and the acquired second authentication information match each other, and limiting execution of at least some functions among a plurality of functions executed in cooperation with the endoscope, in response to determining that the first authentication information and the second authentication information do not match each other.

In another aspect of an embodiment, a function limitation method implemented by an endoscope apparatus that includes a storage memory storing first authentication information. The function limitation method includes acquiring the first authentication information stored in the storage memory, and acquiring, from the endoscope, second authentication information stored in an endoscope connected to the endoscope apparatus, the first authentication information and the second authentication information being different among facilities in which the endoscope and the endoscope apparatus are respectively located; determining whether the acquired first authentication information and the acquired second authentication information match each other; and limiting execution of at least some functions among a plurality of functions executed in cooperation with the endoscope, in response to determining that the first authentication information and the second authentication information do not match each other.

In still another aspect of an embodiment, a non-transitory recording medium having stored therein a computer executable program causing a computer of an endoscope apparatus, which includes a storage memory storing first authentication information, to perform a process including: acquiring the first authentication information stored in the storage memory, and acquiring, from the endoscope, second authentication information stored in an endoscope connected to the endoscope apparatus, the first authentication information and the second authentication information being different among facilities in which the endoscope and the endoscope apparatus are respectively located; determining whether the acquired first authentication information and the acquired second authentication information match each other; and limiting execution of at least some functions among a plurality of functions executed in cooperation with the endoscope, in response to determining that the first authentication information and the second authentication information do not match each other.

BRIEF DESCRIPTION OF DRAWINGS

FIG. 2 illustrates an example of the hardware configuration of a video processor that is an endoscope apparatus in accordance with an embodiment;

FIG. 4 schematically illustrates an example of a change of authentication information (example 2);

FIG. 7 illustrates an example of a situation in which pieces of authentication information match each other.

DESCRIPTION OF EMBODIMENTS

Figure 1:
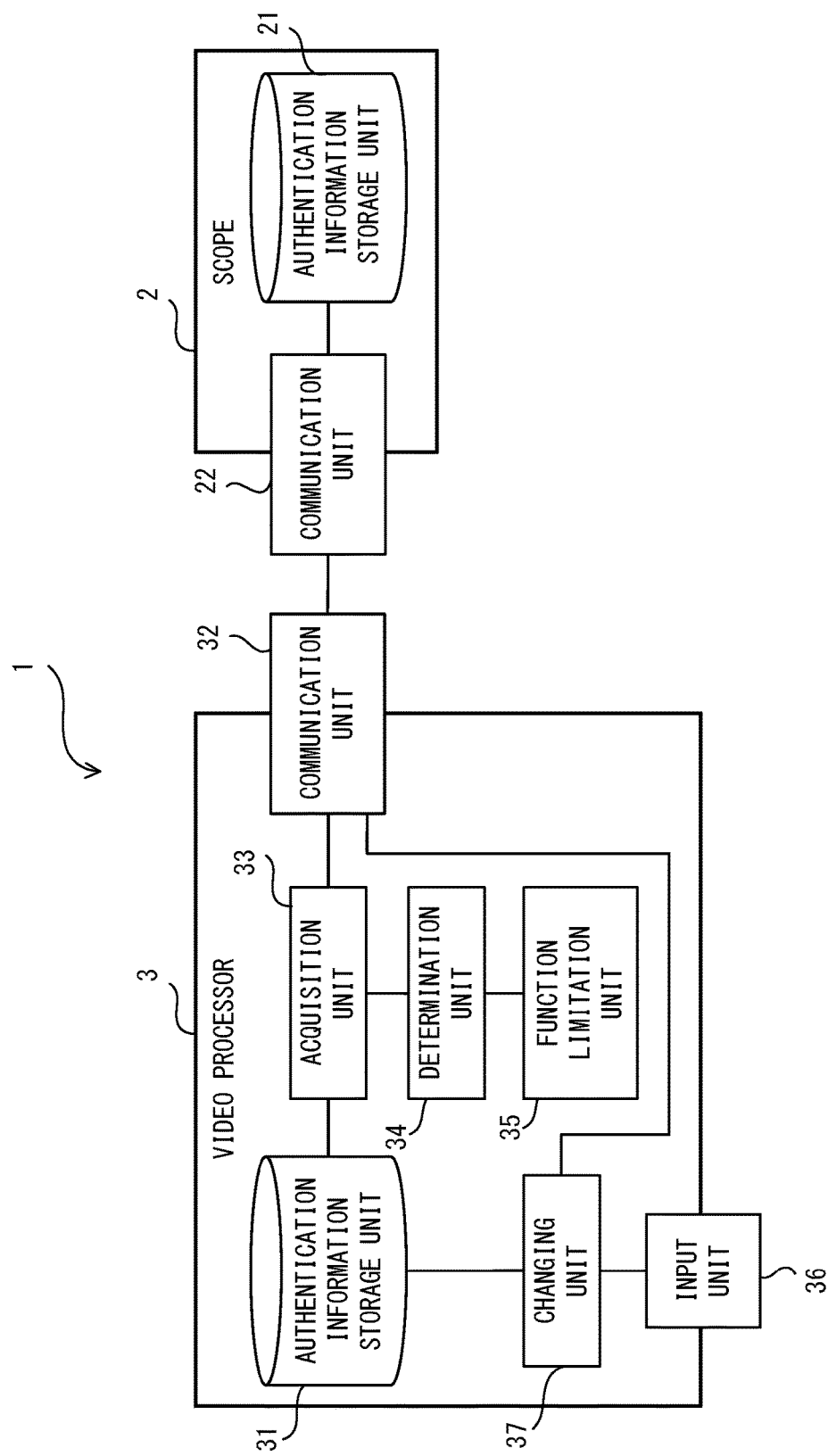
FIG. 1 is a functional block diagram illustrating an example of an endoscope system including a video processor that is an endoscope apparatus in accordance with an embodiment.

An endoscope system can be used when an endoscope and an endoscope apparatus are connected and the operations of the devices are ensured. Thus, there has been a problem that an endoscope system can be used even if an endoscope or an endoscope apparatus is a stolen article.

Accordingly, embodiments disclosed in the following provide an endoscope apparatus, a function limitation method, and a non-transitory recording medium having a program recorded therein, wherein the use can be limited when an endoscope and the endoscope apparatus are connected and one of these is a stolen article.

The following describes embodiments by referring to the drawings.

FIG. 1 is a functional block diagram illustrating an example of an endoscope system including a video processor that is an endoscope apparatus in accordance with an embodiment. However, FIG. 1 depicts main functional blocks pertaining to a function limitation function of the video processor. The function limitation function is, for example, a function for limiting, when one of a scope and a video processor (both described hereinafter) is a stolen article, execution of at least some functions of the functions of the video processor to be executed in cooperation with the scope.

For example, the endoscope system 1 depicted in FIG. 1 may be used in a medical institution such as a hospital.

In FIG. 1, the endoscope system 1 includes a scope 2 that captures an image of the inside of a subject and a video processor 3 that generates a video signal by processing a signal output from the scope 2.

The scope 2 includes an authentication information storage unit 21 and a communication unit 22.

The authentication information storage unit 21 stores authentication information registered for the scope 2. In the present embodiment, blank authentication information is stored in the authentication information storage unit 21 in advance, such as upon factory shipment of the scope 2. The authentication information stored in the authentication information storage unit 21 can be changed, as will be described hereinafter.

The communication unit 22 communicates with the video processor 3, which is connected to the scope 2.

The video processor 3 includes an authentication information storage unit 31, a communication unit 32, an acquisition unit 33, a determination unit 34, a function limitation unit 35, an input unit 36, and a changing unit 37.

The authentication information storage unit 31 stores authentication information registered for the video processor 3. In the present embodiment, blank authentication information is stored in the authentication information storage unit 31 in advance, such as upon factory shipment of the video processor 3. The authentication information stored in the authentication information storage unit 31 can be changed, as will be described hereinafter.

The communication unit 32 communicates with the scope 2 connected to the video processor 3.

The acquisition unit 33 acquires authentication information stored in the authentication information storage unit 31. The acquisition unit 33 also acquires, via the communication units and 22, authentication information stored in the authentication information storage unit 21 of the scope 2 connected to the video processor 3.

Authentication information stored in the authentication information storage unit 31 of the video processor 3 may hereinafter be referred to as first authentication information. Authentication information stored in the authentication information storage unit 21 of the scope 2 may hereinafter be referred to as second authentication information.

The determination unit 34 determines whether the first and second authentication information acquired by the acquisition unit 33 match each other.

The function limitation unit 35 limits execution of at least some functions of the functions to be executed in cooperation with the scope 2 when the determination unit 34 has determined that the first and second authentication information do not match each other. For example, video output to a display apparatus (not illustrated) which is based on a signal input from the scope 2 may be limited. As a result, the video output is not performed.

The input unit 36 inputs first and second authentication information.

The changing unit 37 changes first authentication information stored in the authentication information storage unit 31. However, the change can be made when the input unit 36 has input, prior to this change, first authentication information before change. In particular, when the input unit 36 has input first authentication information before change, the changing unit 37 changes the first authentication information stored in the authentication information storage unit 31 into the first authentication information input by the input unit 36, i.e., the first authentication information after change.

The changing unit 37 also changes second authentication information stored in the authentication information storage unit 21 of the scope 2 via the communication units 32 and 22. However, the change can be made when the input unit 36 has input, prior to this change, second authentication information before change. In particular, when the input unit 36 has input second authentication information before change, the changing unit 37 changes the second authentication information stored in the authentication information storage unit 21 of the scope 2 into the second authentication information input by the input unit 36, i.e., the second authentication information after change.

FIG. 2 illustrates an example of the hardware configuration of a video processor 3 that is an endoscope apparatus in accordance with an embodiment. However, FIG. 2 depicts a hardware configuration pertaining mainly to the functional blocks of the video processor 3 indicated in FIG. 1.

As depicted in FIG. 2, the video processor 3 includes a central processing unit (CPU) 301, a memory 302, an input device 303, an output device 304, a storage device 305, a portable-recording-medium drive device 306 accommodating a portable recording medium 308, and a communication device 307, all of which are connected to each other via a bus 309.

The CPU 301 is an operational device that executes a program for processing performed by the video processor 3. The memory 302 is a random access memory (RAM) and a read only memory (ROM). The RAM is used as a work area or the like for the CPU 301. The ROM stores a program and information necessary for execution of the program in a nonvolatile manner.

The input device 303 is a touch panel, a keyboard, or the like and used to input information or an instruction from a user. The output device 304 is a display device or the like and used to output various setting screens or the like.

The storage device 305 is a storage for storing a program and information necessary for execution of the program, information obtained by executing the program, or the like in a nonvolatile manner. The storage device 305 is a hard disk device or the like. The portable-recording-medium drive device 306 drives the portable recording medium 308, e.g., a memory card, and accesses items recorded therein. As with the storage device 305, the portable recording medium 308 is a storage for storing a program and information necessary for execution of the program, information obtained by executing the program, or the like in a nonvolatile manner.

The communication device 307 is a communication interface device for communicating with the scope 2.

In the hardware configuration depicted in FIG. 2, for example, the acquisition unit 33, the determination unit 34, the function limitation unit 35, and the changing unit 37 illustrated in FIG. 1 may be implemented by the CPU 301 executing a program. The authentication information storage unit 31 depicted in FIG. 1 is implemented by portions of the storage device 305 and the portable recording medium 308. The communication unit 32 depicted in FIG. 1 is implemented by the communication device 307. The input unit 36 depicted in FIG. 1 is implemented by the input device 303.

For example, the acquisition unit 33, the determination unit 34, the function limitation unit 35, and the changing unit 37 depicted in FIG. 1 may be implemented by a circuit such as a field-programmable gate array (FPGA) or an application specific integrated circuit (ASIC).

In the following, processing pertaining to a function limitation function executed in the video processor 3 is described as processing performed in the endoscope system 1.

Figure 3:
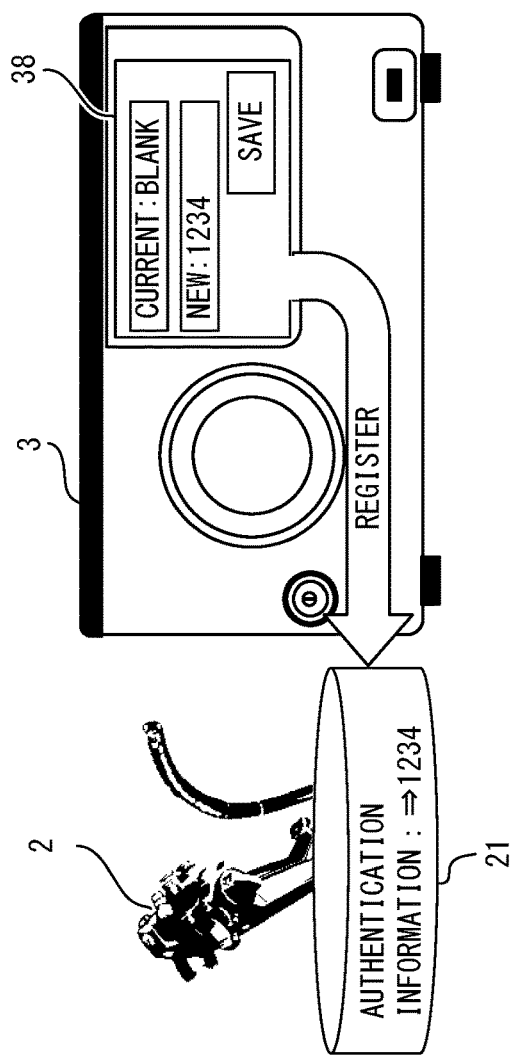
FIG. 3 schematically illustrates an example of a change of authentication information (example 1)
Figure 3:
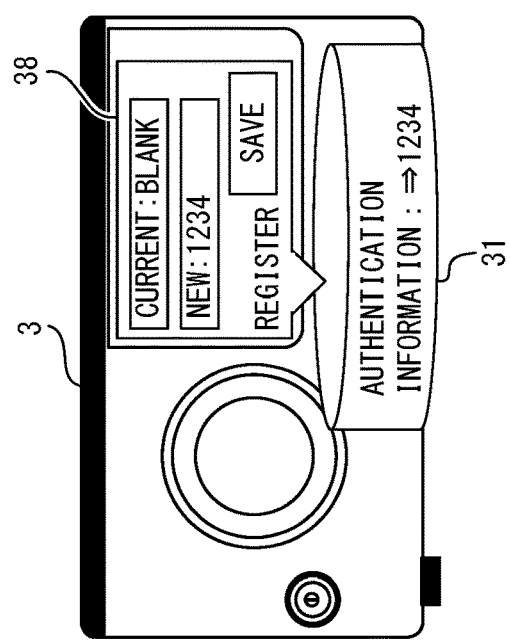

This description is based on the assumption that a user who has validly acquired the scope 2 and the video processor 3 changes pieces of authentication information registered in the scope 2 and the video processor 3 in advance into arbitrary identical authentication information. For example, the pieces of authentication information may be changed from "blank" into "1234", as schematically depicted in FIG. 3. Alternatively, the pieces of authentication information may be changed from "1234" into "5678", as schematically depicted in FIG. 4.

In FIG. 3, "CURRENT: BLANK" on an authentication information setting screen 38 displayed on the video processor 3 indicates a "blank" input by the user as authentication information before change, and "NEW: 1234" indicates a "1234" input by the user as authentication information after change. In FIG. 4, "CURRENT: 1234" on the authentication information setting screen 38 displayed on the video processor 3 indicates a "1234" input by the user as authentication information before change, and "NEW: 5678" indicates a "5678" input by the user as authentication information after change. In FIGS. 3 and 4, a "SAVE" button on the authentication information setting screen 38 displayed on the video processor 3 is a button that is selected by the user when establishing a change of authentication information. Selecting the "SAVE" button triggers the changing of authentication information only when the authentication information before change input by the user matches the authentication information registered at this moment and does not trigger the changing of authentication information when these pieces of authentication information do not match each other. Hence, a person who does not know the authentication information before change, such as a person who has illicitly acquired, e.g., has stolen, the scope 2 or the video processor 3, could not change the authentication information.

Figure 5:
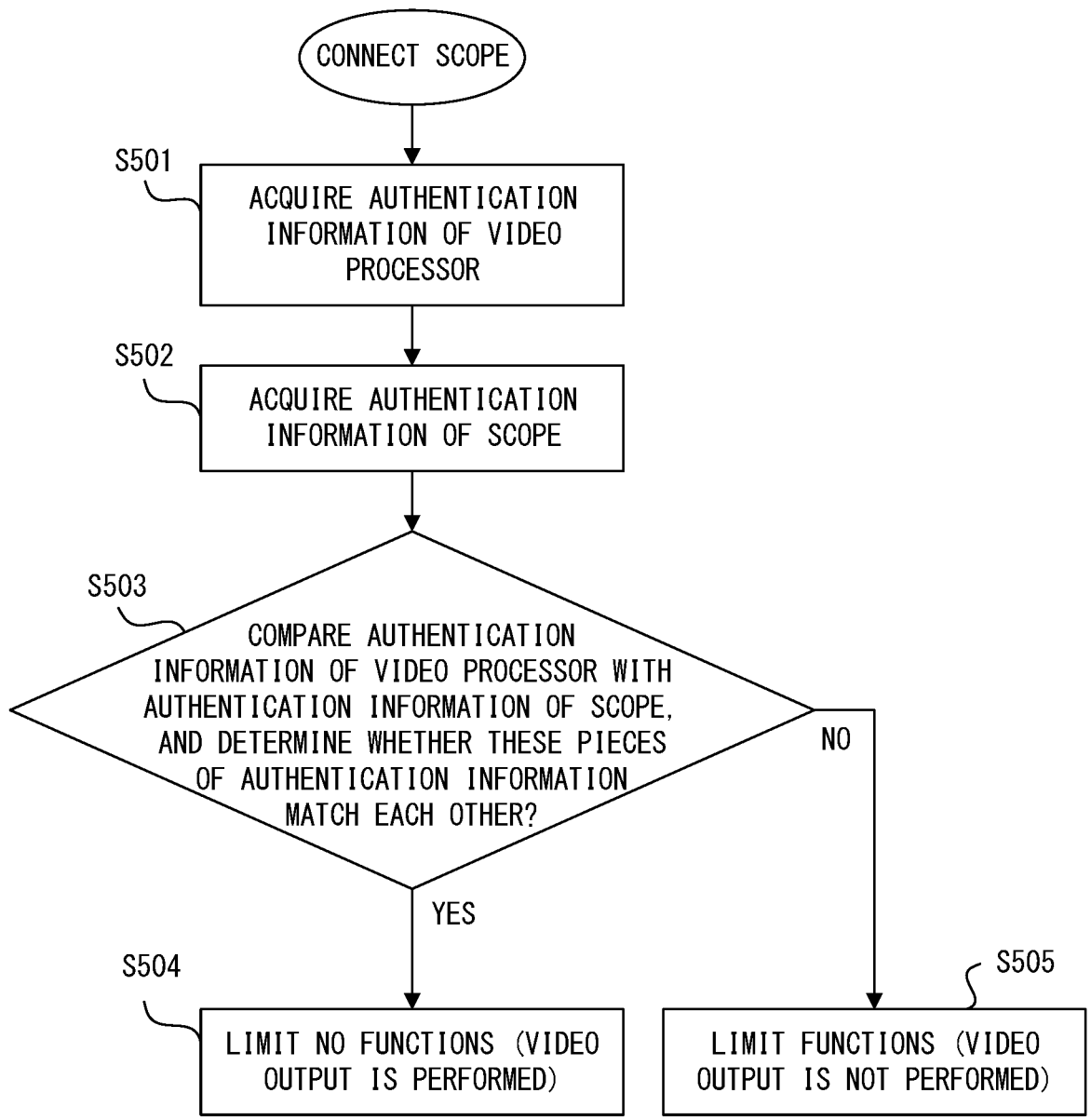
FIG. 5 is a flowchart illustrating an example of a process flow pertaining to a function limitation function executed by a video processor that is an endoscope apparatus in accordance with an embodiment.

FIG. 5 is a flowchart illustrating an example of a process flow pertaining to a function limitation function executed by a video processor 3 that is an endoscope apparatus in accordance with an embodiment.

The processes pertaining to the function limitation function depicted in FIG. 5 start when the scope 2 is connected to the video processor 3.

As depicted in FIG. 5, when the scope 2 is connected to the video processor 3, first, the acquisition unit 33 acquires, via the communication units 32 and 22, second authentication information stored in the authentication information storage unit 21 of the scope 2 connected to the video processor 3 (S501). The acquisition unit 33 acquires first authentication information stored in the authentication information storage unit 31 (S502). In the present embodiment, either the acquiring of first authentication information or the acquiring of second authentication information may be performed first, and then the other may be performed.

Next, the determination unit 34 compares the second authentication information acquired in S501 with the first authentication information acquired in S502 so as to determine whether these pieces of authentication information match each other (S503).

Figure 6:
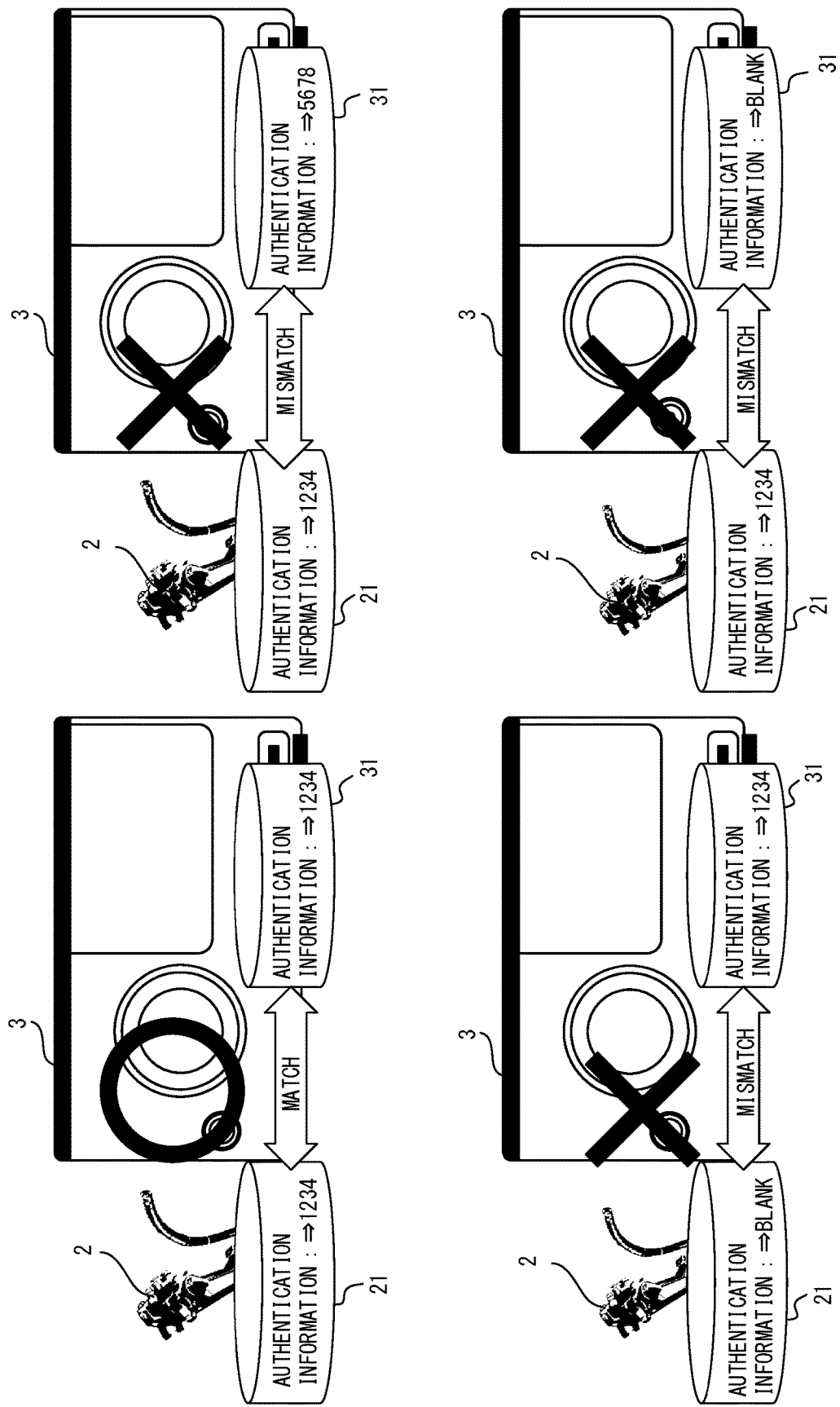
FIG. 6 illustrates examples of a situation in which pieces of authentication information match each other and a situation in which pieces of authentication information do not match each other.

When the determination result from S503 is YES, the function limitation unit 35 does not limit functions to be executed in cooperation with the scope 2 (S504). For example, the functions may not be limited when, as schematically depicted in the upper-left portion of FIG. 6 and in FIG. 7, the second authentication information stored in the authentication information storage unit 21 of the scope 2 matches the first authentication information stored in the authentication information storage unit 31 of the video processor 3. Thus, in this case, all of the functions to be executed in cooperation with the scope 2, such as video output based on a signal input from the scope 2, can be executed.

When the determination result from S503 is NO, the function limitation unit 35 limits execution of at least some functions of the functions to be executed in cooperation with the scope 2 (S505). For example, execution of at least some functions may be limited when, as schematically depicted in the upper-right, lower-left, and lower-right portions of FIG. 6, the second authentication information stored in the authentication information storage unit 21 of the scope 2 does not match the first authentication information stored in the authentication information storage unit 31 of the video processor 3. For example, when execution of video output based on a signal input from the scope 2 is limited as a function of the some functions, the video output will not be performed.

As described above, the present embodiment is such that when one of the scope 2 and the video processor 3 is an illicitly acquired article, such as a stolen article, the first authentication information registered in the video processor 3 and the second authentication information registered in the scope 2 do not match each other, so that execution of at least some functions of the functions of the video processor 3 to be executed in cooperation with the scope 2 can be limited. In this case, if a person who has illicitly acquired the scope 2 or the video processor 3 attempts to change the authentication information so as to remove the limitation, the authentication information cannot be changed since this person does not know the authentication information before change which is required to change the authentication information, i.e., does not know the currently registered authentication information.

In the present embodiment, a user who has validly acquired a scope 2 and a video processor 3 may change pieces of authentication information registered therein into arbitrary identical authentication information, and the arbitrary identical authentication information may be different among facilities in which the scope 2 and the video processor 3 are used. For example, the pieces of registered authentication information may be changed into "1234" for a scope 2 and a video processor 3 used in a facility A, and the pieces of registered authentication information may be changed into "5678" for a scope 2 and a video processor 3 used in a facility B. As a result, when, for example, a scope 2 or a video processor 3 stolen from the facility A is used in the facility B, execution of at least some functions of the functions of the video processor 3 to be executed in cooperation with the scope 2 can be limited.

In the present embodiment, when pieces of authentication information registered in the scope 2 and the video processor 3 do not match each other, execution of all of the functions of the video processor 3 to be executed in cooperation with the scope 2 may be limited. In this case, none of the functions of the video processor 3 to be executed in cooperation with the scope 2 can be executed.

The present embodiment(s) is not simply limited to the embodiments described herein. Components of the embodiments may be embodied in a varied manner in an implementation phase without departing from the gist of the embodiment(s). A plurality of components disclosed with reference to the described embodiments may be combined, as appropriate, to achieve various embodiments. For example, some of the components indicated with reference to embodiments may be omitted. In addition, components of different embodiments may be combined as appropriate.

What is claimed is:

1. An endoscope apparatus comprising:
   a storage memory that stores first authentication information;
   a transmitter/receiver that performs communication with an endoscope connected to the endoscope apparatus; and
   a processor configured to:
      acquire the first authentication information stored in the storage memory and acquiring, from the endoscope, second authentication information stored in the endoscope connected to the endoscope apparatus, the first authentication information and the second authentication information being different among facilities in which the endoscope and the endoscope apparatus are respectively located,
      determine whether the acquired first authentication information and the acquired second authentication information match each other, and
      limit execution of at least some functions among a plurality of functions executed in cooperation with the endoscope, in response to determining that the first authentication information and the second authentication information do not match each other, wherein when the second authentication information is input prior to the processor modifying the second authentication information, the processor modifies the second authentication information stored in the endoscope connected to the endoscope apparatus.

2. The endoscope apparatus of claim 1, wherein the processor is configured to:
   inputs the first authentication information and the second authentication information.

3. The endoscope apparatus of claim 2, wherein the process performed by the processor further includes modifying the first authentication information stored in the storage memory.

4. The endoscope apparatus of claim 3, wherein when first authentication information is input to the processor, the processor modifies the first authentication information stored in the storage memory.

5. The endoscope apparatus of claim 3, wherein the processor modifies the second authentication information stored in the endoscope connected to the endoscope apparatus.

6. The endoscope apparatus of claim 1, wherein the processor limits, as a function of the plurality of functions to be executed in cooperation with the endoscope, video output to a display apparatus that is based on a signal input from the endoscope.

7. A function limitation method implemented by an endoscope apparatus that includes a storage memory storing first authentication information, the function limitation method comprising:
   acquiring the first authentication information stored in the storage memory, and acquiring, from the endoscope, second authentication information stored in an endoscope connected to the endoscope apparatus, the first authentication information and the second authentication information being different among facilities in which the endoscope and the endoscope apparatus are respectively located;
   determining whether the acquired first authentication information and the acquired second authentication information match each other; and
   limiting execution of at least some functions among a plurality of functions executed in cooperation with the endoscope, in response to determining that the first authentication information and the second authentication information do not match each other, wherein the processor modifies the second authentication information after the processor determines that the second authentication information matches the first authentication information.

8. A non-transitory computer readable recording medium having stored therein a computer executable program causing a computer of an endoscope apparatus, which includes a storage memory storing first authentication information, to perform a process comprising:
   acquiring the first authentication information stored in the storage memory, and acquiring, from the endoscope, second authentication information stored in an endoscope connected to the endoscope apparatus, the first authentication information and the second authentication information being different among facilities in which the endoscope and the endoscope apparatus are respectively located;
   determining whether the acquired first authentication information and the acquired second authentication information match each other; and
   limiting execution of at least some functions among a plurality of functions executed in cooperation with the endoscope, in response to determining that the first authentication information and the second authentication information do not match each other, wherein when the second authentication information is input prior to the processor modifying the second authentication information, the processor modifies the second authentication information stored in the endoscope connected to the endoscope apparatus.

9. The endoscope apparatus of claim 1, wherein the processor modifies the second authentication information after the processor determines that the second authentication information matches the first authentication information.

10. The function limitation method of claim 7, wherein the processor modifies the second authentication information after the processor determines that the second authentication information matches the first authentication information.

11. The non-transitory computer readable recording medium of claim 8, wherein the processor modifies the second authentication information after the processor determines that the second authentication information matches the first authentication information.

* * * * *